United States Patent [19]

Whistler

[11] 4,298,726

[45] Nov. 3, 1981

[54] SYNTHESIS OF N-BENZOYL-L-RISTOSAMINE AND INTERMEDIATES USED IN ITS PREPARATION

[75] Inventor: Roy L. Whistler, West Lafayette, Ind.

[73] Assignee: Purdue University, West Lafayette, Ind.

[21] Appl. No.: 128,298

[22] Filed: Mar. 7, 1980

[51] Int. Cl.³ .............................................. C07H 15/04
[52] U.S. Cl. .............................. 536/4; 260/345.8 R; 536/1; 536/18; 536/53; 424/180
[58] Field of Search .......................... 536/1, 4, 18, 53; 260/345.8 R

[56] References Cited

U.S. PATENT DOCUMENTS

| | | | |
|---|---|---|---|
| 3,953,422 | 4/1976 | Pfeiffer | 536/4 |
| 4,020,270 | 4/1977 | Arcamone et al. | 536/17 A |
| 4,024,333 | 5/1977 | Horton et al. | 536/4 |
| 4,112,076 | 9/1978 | Arcamone et al. | 536/17 A |
| 4,181,795 | 1/1980 | Whistler | 536/17 A |

OTHER PUBLICATIONS

Arcamone, et al., "Synthesis of a Configurational Analog of Daunorubicin" 46 *Carbohydrate Research* C3–C5 (1976).
Sztaricskai et al., "The Synthesis of N-Benzoylristosamine" 13 *Tetrahedron Letters*, 1111–1114 (1975).
Bargiotti et al., *Carbohydrate Research*, 58 pp. 353–361, (1977).
Iselin et al., *Helvetica Chimica. Acta.* 27 p. 1146 (1944).
Baer et al., *Carbohydrate Research*, 55, pp. 253–258, 1977.
Pelyvas et al., *Carbohydrate Research*, 53, C17–C19 (1977).
Lee et al., *Jour. of Medicinal Chem.* 18, p. 767, (1975).
Tanaka, "Carbohydrates", 33, p. 51, para. 91:5437 m 1979.

*Primary Examiner*—Johnnie R. Brown
*Attorney, Agent, or Firm*—Finnegan, Henderson, Farabow, Garrett & Dunner

[57] ABSTRACT

A process for synthesizing N-benzoyl-L-ristosamine is disclosed. Intermediates useful for synthesizing N-benzoyl-L-ristosamine, and processes for preparing such intermediates, are also disclosed.

19 Claims, No Drawings

SYNTHESIS OF N-BENZOYL-L-RISTOSAMINE AND INTERMEDIATES USED IN ITS PREPARATION

FIELD OF THE INVENTION

The present invention pertains to a technique for synthesizing N-benzoyl-L-ristosamine and intermediates which can be converted into N-benzoyl-L-ristosamine. The present invention also pertains to certain novel intermediates useful in the synthesis of N-benzoyl-L-ristosamine.

BACKGROUND OF THE INVENTION

Daunomycin, a known anthracycline antibiotic, is an antineoplastic agent of established clinical utility. Daunomycin consists of the aglycone, daunomycinone, and the amino sugar, daunosamine. A process for synthesizing daunosamine hydrochloride, as well as certain novel intermediates, is disclosed in U.S. Patent Application Ser. No. 128,299, filed concurrently herewith.

3',4'-epi-daunomycin consists of the aglycone, daunomycinone, and the amino sugar, ristosamine. 3',4'-epi-daunomycin has the formula:

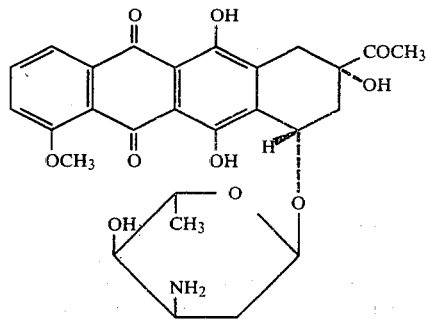

3',4'-epi-daunomycin, like daunomycin, exhibits antitumor activity. See Arcamone et al., Synthesis of a Configurational Analog of Daunorubicin, Carbohydrate Research, Vol. 46, p. c3 (1976); Bargiotti et al., Synthesis of Derivatives of 3-Amino-2,3-dideoxy-L-hexoses Related to Daunosamine (3-Amino-2,3,6-Trideoxy-L-lyxohexose), Carbohydrate Research, Vol. 58, p. 353 (1977). Specifically, 3',4'-epi-daunomycin is effective against P-388 leukemia in mice. See U.S. Pat. No. 4,112,076 to Arcamone et al.

Since the amino sugar, ristosamine, provides an important part of 3',4'-epi-daunomycin, techniques for synthesizing ristosamine, and related compounds, are highly desirable as part of a technique for the total synthesis of 3',4'-epi-daunomycin.

Techniques for synthesizing L-ristosamine and related compounds are known. See, e.g., Lee et al., Confirmation by Synthesis of Ristosamine as 3-Amino-2,3,6-trideoxy-L-ribohexose, Journal of Medicinal Chemistry, Vol. 18, No. 7, p. 767 (1975); Sztaricskai et al., The Synthesis of N-Benzoylristosamine, Tetrahedron Letters, No. 13, p. 1111 (1975). Moreover, techniques for synthesizing D-ristosamine, an enantiomer of L-ristosamine, are also known. See, e.g., Pelyvas et al., A New Synthesis of D-ristosamine Derivatives, Carbohydrate Research, Vol. 53, p. c17 (1977); Baer et al., A Synthesis of 3-Amino-2,3,6-trideoxy-D-ribo-hexose (D-ristosamine) hydrochloride, Carbohydrate Research, Vol. 55, p. 253 (1977).

The techniques for synthesizing L-ristosamine disclosed by Lee et al., supra, and Sztaricskai et al., supra, both involve the potentially hazardous step of making an azide derivative with sodium azide. Moreover, in Sztaricskai et al. the reduction of the azide group to the amino group has a yield of only 36%.

The present invention provides a practical technique for synthesizing N-benzoyl-L-ristosamine. In addition, the present invention provides novel intermediates, and methods for their preparation, useful in synthesizing N-benzoyl-L-ristosamine.

SUMMARY OF THE INVENTION

In accordance with the present invention, the known compounds, L-rhamnal or 6-deoxy-L-allal, are used as starting materials to produce alkyl L-ristosaminides. These latter compounds may be converted to the known compound N-benzoyl-L-ristosamine.

The process of the present invention for synthesizing alkyl L-ristosaminides involves:

a. oxidizing either L-rhamnal or 6-deoxy-L-allal;

b. reacting the resultant 1,5-anydro-3-oxo-2,3,6-trideoxy-L-erythro-hex-1-enitol with a blocking agent to produce a compound having the formula

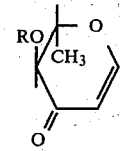

wherein R is a blocking group;

c. subjecting the resultant compound to alkyloxymercuration to produce a ketose having the formula

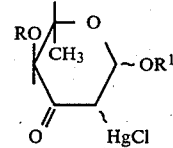

wherein $R^1$ is $C_1$–$C_6$ alkyl;

d. subjecting the resultant ketose to oximation to produce an oxime having the formula

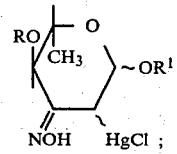

e. demercurating the oxime to a compound having the formula

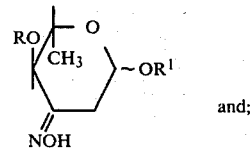

and;

f. reducing the resultant compound with simultaneous removal of the blocking group to produce alkyl L-ristosaminides.

The L-rhamnal used in step (a) may be prepared by deacetylating 3,4-di-O-acetyl-L-rhamnal to produce L-rhamnal.

While the compound produced by step (e) can be directly reduced with simultaneous removal of the blocking group, it is preferable to first react it with a blocking agent to produce a compound having the formula

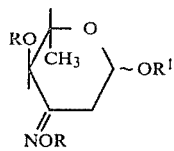

wherein R is a blocking group, and then reducing the resultant compound with simultaneous removal of the blocking groups to produce alkyl L-ristosaminides.

The alkyl L-ristosaminides produced by the above-described process may be converted to N-benzoyl-L-ristosamine by benzoylating alkyl L-ristosaminides, and subjecting the resultant alkyl N-benzoyl-L-ristosaminides to acid hydrolysis. As an alternative, the alkyl L-ristosaminides may be hydrolyzed to L-ristosamine hydrochloride by the procedure described in Lee et al., supra.

The present invention also pertains to novel intermediates, and methods for their preparation, useful in synthesizing N-benozyl-L-ristosamine. Among such intermediates are those having the formula:

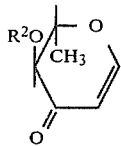

wherein R² is

The present invention additionally provides valuable intermediates, and methods for their preparation, useful in synthesizing N-benzoyl-L-ristosamine including those having the formula:

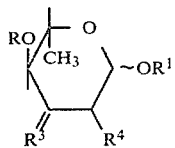

wherein
R is

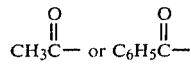

R¹ is C₁–C₆ alkyl
R³ is

R⁴ is HgCl or H
provided that when R⁴ is HgCl, R³ must be O= or HON=; when R⁴ is H, R³ cannot be O=.

DESCRIPTION OF PREFERRED EMBODIMENTS

In the synthesis technique of the present invention, the known compound, 3,4-di-O-acetyl-L-rhamnal may be used as a starting material. Its preparation is described in Iselin et al., Krystallisierte 2-Deoxy-l-rhamnose (2-Desoxy-l-chinovose), Helvetica Chimica Acta, Vol. 27, p. 1146 (1944). The compound, 3,4-di-O-acetyl-L-rhamnal has the formula:

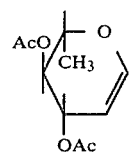

1.

Parenthetically, in the above structural formula, as well as in other structural formulas appearing herein, some of the hydrogen atoms are omitted for the sake of clarity, and "Ac" is used to represent the acetyl radical, i.e.,

Those skilled in the art will have no trouble withstanding these formulas. The compound of formula 1 is deacetylated to produce L-rhamnal having the formula:

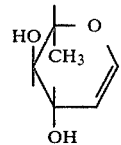

2.

Deacetylation is preferably effected by dissolving the formula 1 compound in methanol, and adjusting the pH to 8 to 9 by the addition of sodium methoxide in methanol. The solution is neutralized and the solvent is removed under reduced pressure. The resulting clear syrup is co-evaporated with toluene several times, and the syrup crystallizes during these evaporations.

Either the compound of formula 2 or 6-deoxy-L-allal, which is prepared by the procedure of F. Michael, Chem. Ber., Vol. 63, p. 347 (1930) (describes preparation of corresponding D-isomer), and which has the formula:

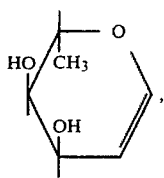

are oxidized to produce 1,5-anhydro-3-oxo-2,3,6-trideoxy-L-erythro-hex-1-enitol having the formula:

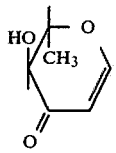
3.

Oxidation is preferably conducted by dissolving either the compound of formula 2 or 2' in benzene, and then adding silver carbonate on celite (Fetizon's reagent). The mixture is distilled to remove part of the solvent, and then refluxed. The mixture is then filtered through celite, and the filtrate is evaporated giving the crude crystalline compound of formula 3. This compound may be freed from any unreacted compound of formula 2 or 2' by recrystallization or by separating the mixture between chloroform and water.

The Fetizon's reagent used in the above oxidation step is prepared by dissolving silver nitrate in distilled water, adding celite, and then adding a solution of potassium bicarbonate in distilled water. The well-stirred suspension is filtered to collect the reagent, which reagent is stored in a brown glass bottle at room temperature.

As an alternative preferable oxidation step, either the compound of formula 2 or 2' can be reacted with a specially prepared suspension of manganese dioxide in tetrahydrofuran. The manganese dioxide used in this step is prepared by dissolving potassium permanganate in distilled water, heating, and adding simultaneously manganese sulfate monohydrate in water and a solution of sodium hydroxide. The suspension is stirred, filtered, and washed. The resultant chocolate-brown solid is then dried to produce a manganese dioxide satisfactory for use in the oxidation step.

As a further alternative preferable oxidation step, either the compound of formula 2 or 2' can be reacted with chromium trioxide:pyridine complex in methylene chloride catalyzed by acetic anhydride.

The compound of formula 3 is then reacted with a blocking agent to produce a compound having the formula:

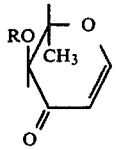
4.

where R is a blocking group.

Examples of suitable blocking groups which may be used throughout the present synthesis technique include acetyl

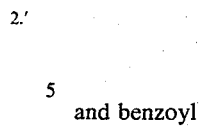

and benzoyl

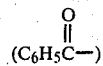

groups. These groups may be introduced by reacting the compound of formula 3 with, respectively, such compounds as acetic anhydride or benzoyl chloride. The reaction is preferably conducted in a solvent which is a good acid receptor, such as pyridine, sodium hydroxide solution, or quinoline. The solvent is subsequently evaporated, and the residue co-evaporated several times with toluene. When the preferred reactant, acetic anhydride, is reacted with the compound of formula 3, 1,5-anydro-3-oxo-4-O-acetyl-2,3,6-trideoxy-L-erythro-hex-1-enitol is produced.

The compound of formula 4 is next subjected to alkyloxymercuration to produce a ketose having the formula:

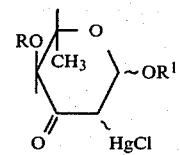
5.

wherein R is a blocking group as previously defined and $R^1$ is $C_1$–$C_6$ alkyl. When R is the preferred acetyl group and $R^1$ is methyl, this compound would be methyl 2-chloromercuri-3-oxo-4-O-acetyl-2,3,6-trideoxy-L-(ribo arabino)-hexopyranoside. Methoxymercuration is preferably conducted by dissolving mercuric acetate and mercuric chloride in methanol, refluxing the mixture, and cooling to room temperature. The compound of formula 4, as a solution in methanol, is then added to the refluxed mixture. The mixture is stirred at room temperature, and then the solvent is evaporated under reduced pressure. The residue is coevaporated with toluene to remove the acetic acid formed in the reaction, and the remaining residue is dissolved in chloroform and filtered to remove any chloroform-insoluble matter. Evaporation of the filtrate yields the compound of formula 5 as a mixture of stereoisomers.

The ketose of formula 5 is then subjected to oximation to produce an oxime having the formula:

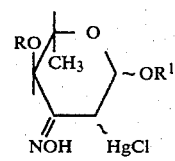
6.

wherein R and $R^1$ are as previously described. When R is the preferred acetyl group and $R^1$ is methyl, this compound would be methyl 2-chloromercuri-3-oximino-4-O-acetyl-2,3,6-trideoxy-L-(ribo, arabino)-hexopyranoside. Oximation can be effected by reacting the ketose of formula 5 with hydroxylamine.

The compound of formula 6 is next subjected to demercuration to produce a compound having the formula:

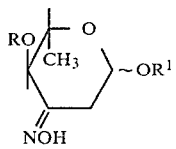

7.

wherein R and R¹ are as previously defined. When R is the preferred acetyl group and R¹ is methyl, the compound would be methyl 3-oximino-4-O-acetyl-2,3,6-trideoxy-L-erythrohexopyranoside. Preferably, demercuration is effected by dissolving the compound of formula 6 in methanol, and adding triethylamine followed by sodim borohydride. The suspension is filtered through celite to remove elemental mercury, and the filtrate then evaporated. The residue is slurried in hot diethyl ether and filtered to remove triethylammonium chloride. The filtrate is evaporated to produce the compound of formula 7 in the form of a syrup.

While the oxime of formula 7 could be directly reduced with simultaneous removal of the blocking group to produce alkyl L-ristosaminides, it is preferable to first react it with a blocking agent to produce a compound having the formula:

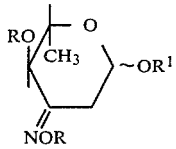

8.

wherein R and R¹ are as previously defined. The blocking agent can be the same as those reacted with the compound of formula 3, namely, acetic anhydride or benzoyl chloride. As with the previously described reaction involving the formula 3 compound, the reaction involving the oxime of formula 7 is preferably conducted in a solvent which is a good acid receptor, such a pyridine, sodium hydroxide solution, or quinoline. The solvent is subsequently evaporated, and the residue co-evaporated several times with toluene. When the preferred reactant, acetic anhydride, is reacted with the preferred oxime of formula 7, and when R¹ is methyl, methyl 3-acetyloximino-4-O-acetyl-2,3,6-trideoxy-L-erythro-hexopyranoside is produced.

The compound of formula 8 is next reduced with simultaneous removal of the blocking groups to produce alkyl L-ristosaminides having the formula:

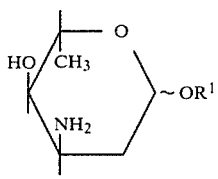

9.

When R¹ is methyl, this compound is methyl L-ristosaminide. The reduction is preferably effected by dissolving the formula 8 compound in tetrahydrofuran, and then adding, as the reducing agent, lithium aluminum hydride, followed by refluxing. The solution is then cooled to room temperature, and excess hydride destroyed with water and 1 N sodium hydroxide. The insoluble material is filtered, and the filtrate evaporated to produce the compound of formula 9 in the form of a syrup.

The compound of formula 9 may, if desired, be converted to N-benzoyl-L-ristosamine. This conversion is effected in two steps. First, the compound of formula 9 is converted to alkyl N-benzoyl-L-ristosaminide having the formula:

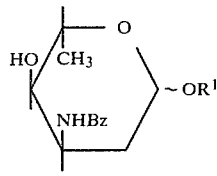

10.

In the above formula, as elsewhere herein, "Bz" is used to represent the benzoyl radical, i.e.,

The conversion can be effected by dissolving the compound of formula 9 in water, adding potassium bicarbonate, cooling the solution, and then adding a solution of benzoyl chloride in acetone. Subsequent to the reaction, the acetone is evaporated and the remaining aqueous suspension washed with chloroform. The combined chloroform extracts are dried, filtered, and evaporated to give the compound of formula 10 in the form of a syrup.

The second step in the conversion of alkyl L-ristosaminides to N-benzoyl-L-ristosamine involves the acid hydrolysis of the compound of formula 10 to produce N-benzoyl-L-ristosamine having the formula:

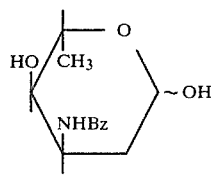

11.

The acid hydrolysis is effected by dissolving the compound of formula 10 in a mixture of water and glacial acetic acid, refluxing, and evaporating the solvent. The residue is then co-evaporated several times with a toluene to give the crude compound of formula 11. Partial purification is effected by a hot water extraction of the crude product.

The alkyl L-ristosaminides can be used in a process for producing 3',4'-epi-daunomycin. Specifically, methyl L-ristosaminide is reacted with trifluoroacetic anhydride, in the manner described by Sztaricskai et al., A Synthesis of L-ristosamine and a Derivative of its C-4 Epimer, Carbohydrate Research, Vol. 65, p. 193 (1978), to produce methyl N,O-ditrifluoroacetyl-L-ristosaminide, the trifluoroacetyl group then being selectively removed from the 4-position. This product is then allowed to react with p-nitrobenzoyl chloride as described by Arcamone et al., Synthesis of a Configurational Analog of Daunorubicin, supra. Acid hydrolysis followed by p-nitrobenzoylation of the resulting free sugar, and subsequent treatment with dry hydrogen chloride, gives 4-O-p-nitrobenzoyl-3-N-trifluoroacetyl-2,3,6-trideoxy-L-ribo-hexopyranosyl chloride. The latter may then be condensed with the aglycone, daunomycinone, to give, after removal of the blocking groups, 3′,4′-epi-daunomycin.

The following examples further illustrate preferred embodiments of the invention. The examples should in no way be considered limiting, but are merely illustrative of the various features of the present invention.

EXAMPLE 1

10 grams of 3,4-di-O-acetyl-L-rhamnal is dissolved in 100 milliliters of methanol, and the pH is adjusted to 8 to 9 by the dropwise addition of a freshly prepared solution of sodium methoxide in methanol. The flask is sealed and allowed to stand at 0°–5° C. overnight after which time deacetylation is complete. The solution is neutralized by the careful dropwise addition of glacial acetic acid, and then the solvent is removed under reduced pressure. The resulting clear syrup is coevaporated several times with toluene to remove any excess acetic acid, and the syrup crystallizes during these evaporations to give L-rhamnal. The yield of this compound is 6 grams.

EXAMPLE 2

In a flask equipped for distillation, 1 grams of L-rhamnal [Example 1 product] is dissolved in 100 milliliters of benzene. To this solution was added 20–25 grams of silver carbonate on celite (Fetizon's reagent), prepared as described below. The mixture is distilled to remove 20–25 milliliters of the solvent, and then the dark brown suspension is refluxed for 1 to 2 hours. The mixture is then filtered through celite, and the solvent is evaporated. Crude 1,5-anydro-3-oxo-2,3,6-trideoxy-L-erythrohex-1-enitol crystallizes on the walls of the flask, and may be freed from a small amount of unreacted L-rhamnal by recrystallization or by separating the mixture between chloroform and water. The yield of the product is 0.9 grams.

Preparation of Fetizon's Reagent

In 200 milliliters of distilled water is dissolved 34 grams of silver nitrate, followed by 30 grams of celite. Then, cautiously and in several portions, is added a solution of 21 grams of potassium bicarbonate in 300 milliliters of distilled water. Ten minutes after the final addition of the bicarbonate solution, the well-stirred suspension is filtered to collect the reagent. The reagent is air-dried for 15–30 minutes and then transferred to a 1 liter flask and put on a rotary evaporator for several hours to remove most of the water. The yield of Fetizon's reagent was 58 grams. The reagent is stored in a brown glass bottle to protect it from light and left at room temperature.

EXAMPLE 3

As an alternative to the procedure of Example 2, 1 gram of L-rhamnal may be oxidized by 15–20 grams of specially prepared manganese dioxide (described below) in tetrahydrofuran at room temperature. As with the procedure of Example 2, the product is 1,5-anhydro-3-oxo-2,3,6-trideoxy-L-erythro-hex-1-enitol.

Preparation of Activated Manganese Dioxide 48 grams of potassium permanganate in 300 milliliters of distilled water was heated to 90° C. To this solution was added simultaneously 42 grams of manganese sulfate monohydrate in 75 milliliters of water and 60 milliliters of B 40% sodium hydroxide over a period of 15–20 minutes. The suspension was stirred at 85°–90° C. for 1 hour, filtered, and washed with water until the washings are clear. The chocolate-brown solid is dried overnight at 160° C. to yield 41 grams of manganese dioxide.

EXAMPLE 4

As a second alternative to the procedure of Example 2, 4 grams of chromium trioxide is added to a solution of methylene chloride containing 1.61 milliliters of pyridine and the mixture is stirred at 25° C. for 15 minutes. To this solution is added 1.3 grams of L-rhamnal immediately followed by the addition of 0.95 milliliters of acetic anhydride, the reaction being monitored by t.l.c. The reaction is generally complete in 5–10 minutes. The reaction mixture is then poured onto a silica gel column which has an amount of ethyl acetate above it to precipitate the chromium compounds, and the product is eluted as one fraction. The resulting 1,5-anhydro-3-oxo-2,3,6-trideoxy-L-erythro-hex-1-enitol is purified by recrystallization.

EXAMPLE 5

The procedure identical to that described in Examples 2, 3 or 4 may be followed, except that 6-deoxy-L-allal is substituted for L-rhamnal. The same product (1,5-anhydro-3-oxo-2,3,6-trideoxy-L-erythro-hex-1-enitol) is formed.

EXAMPLE 6

0.9 grams of the compound produced in Examples 2–5 (1,5-anhydro-3-oxo-2,3,6-trideoxy-L-erythro-hex-1-enitol) is dissolved in 20 milliliters of acetic anhydride pyridine (1:1), and the mixture is shaken overnight. The solvent is then evaporated and the residue coevaporated several times with toluene to remove the last traces of acetic anhydride, pyridine, and/or water. The yield of the product, 1,5-anhydro-3-oxo-4-O-acetyl-2,3,6-trideoxy-L-erythro-hex-1-enitol, is 1.1 grams.

EXAMPLE 7

1.5 grams of mercuric acetate, freshly recrystallized from water, and 1.2 grams of mercuric chloride are dissolved/suspended in 200 milliliters of methanol, and the mixture is refluxed for 1 to 1.5 hours. The solution is cooled to room temperature, and 1.1 grams of the compound produced in Example 6 is added as a methanolic solution. This mixture is stirred for 1.5 to 2 hours at room temperature, and the solvent is then evaporated under reduced pressure. The residue is co-evaporated with toluene to remove the acetic acid formed in the reaction. Crude methyl 2-chloromercuri-3-oxo-4-O-acetyl-2,3,6-trideoxy-L-erythro-hexopyranoside forms a foam on evaporation. The residue is dissolved in chloroform and filtered to remove any chloroforminsoluble matter. Evaporation of the filtrate leads to, as a mixture of stereoisomers, methyl 2-chloromercuri-3-oxo-4-O-acetyl-2,3,6-trideoxy-L-(ribo, arabino)-hexopyranoside. The yield of this product is 3.1 grams.

EXAMPLE 8

3.2 grams of hydroxylamine hydrochloride, freshly recrystallized from methanol, and 2.6 grams of potassium hydroxide are reacted in 200 milliliters of absolute ethanol. After 30 minutes the precipitated potassium chloride is filtered and the compound produced in Example 7 is added to the hydroxylamine solution as a solution in absolute ethanol. The flask is stoppered and the mixture is stirred overnight. The ethanol is then evaporated under reduced pressure and the powdery white solid is co-evaporated with toluene to remove excess solvent, water, etc. The yield of the product, methyl 2-chloromercuri-3-oximino-4-O-acetyl-2,3,6-trideoxy-L-(ribo, arabino)-hexpyranoside is 3.4 grams.

EXAMPLE 9

The compound produced in Example 8 was suspended in methanol and cooled to 0° C. Quickly thereafter, 3.7 milliliters of triethylamine is added followed immediately by 150 milligrams of sodium borohydride, added in several portions. Immediate demercuration and hydrogen evolution were noted. The solution was stirred for 1.5 hours while slowly allowing it to come to room temperature. The suspension was filtered through celite to remove the mercury, and the filtrate was evaporated under reduced pressure. The residue was slurried in hot diethyl ether and filtered to remove the insoluble triethylammonium chloride. The filtrate was evaporated under reduced pressure to yield 1.2 grams of methyl 3-oximino-4-O-acetyl-2,3,6-trideoxy-L-erythro-hexopyranoside.

EXAMPLE 10

1.2 grams of the compound produced in Example 9 is dissolved in 20 milliliters of acetic anhydride:pyridine (1:1) and stirred overnight at room temperature. The solvent was then evaporated and the residue was co-evaporated with toluene to remove the last traces of acetic anhydride and pyridine. The yield of the product, methyl 3-acetyloximino-4-O-acetyl-2,3,6-trideoxy-L-erythro-hexopyranoside, is essentially quantitative. This product will crystallize as long needles from a slowly evaporating chloroform solution.

EXAMPLE 11

The compound produced in Example 10 is dissolved in 100 milliliters of tetrahydrofuran at 0° C., and the solution is de-gassed by bubbling dry nitrogen through it for 10–15 minutes. 0.55 grams of lithium aluminum hydride is then carefully added in several portions. The reaction is allowed to proceed under nitrogen at 0° C. for 30 minutes and is then brought to a reflux under nitrogen. Reflux is maintained for 1.5 to 2 hours, after which the solution is cooled to room temperature and the excess hydride carefully destroyed with water and 1 N sodium hydroxide. The insoluble material is filtered and the filtrate is evaporated under reduced pressure to yield 0.85 grams of methyl L-ristosaminide as a syrup.

EXAMPLE 12

0.85 grams of methyl L-ristosaminide [Example 11 compound] was dissolved in 30–40 milliliters of water, and to this solution was added 4 grams of potassium bicarbonate. The solution was cooled to 0° C. and to it was added a solution of 1.5 milliliters of benzoyl chloride in 20 milliliters of acetone. The reaction was allowed to proceed at 0° C. for 2 to 3 hours, and then reacted at room temperature for 16 to 18 hours. At the end of this time the acetone was evaporated from the mixture and the remaining aqueous suspension was washed with three separate 50 milliliter portions of chloroform. The combined chloroform extracts were dried over magnesium sulfate, filtered, and evaporated under reduced pressure to yield 0.95 grams of methyl N-benzoyl-L-ristosaminide as a syrup.

EXAMPLE 13

0.95 grams of the compound produced in Example 12 was dissolved/suspended in a mixture of 30 milliliters of water and 6 milliliters of glacial acetic acid. The mixture was refluxed for 45 minutes and the solvent was then evaporated and the residue co-evaporated several times with toluene. Partial purification of this material was effected by a hot water extraction of the residue to yield N-benzoyl-L-ristosamine. Although some difficulty is encountered, this material can be obtained in crystalline form.

What is claimed is:

1. A process for making alkyl L-ristosaminides comprising:
   a. oxidizing either L-rhamnal or 6-deoxy-L-allal;
   b. reacting the resultant 1,5-anydro-3-oxo-2,3,6-trideoxy-L-erythro-hex-1-enitol with a blocking agent to produce a compound having the formula

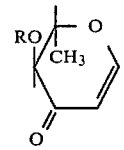

wherein R is a blocking group;
   c. subjecting the resultant compound to alkyloxymercuration to produce a ketose having the formula

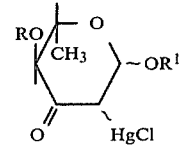

wherein $R^1$ is $C_1$–$C_6$ alkyl;
   d. subjecting the resultant ketose to oximation to produce an oxime having the formula

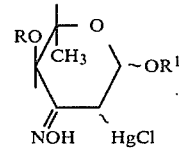

e. demercurating the oxime to a compound having the formula

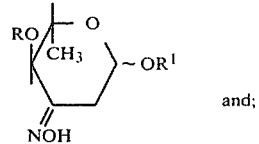

and;

f. reducing the resultant compound with simultaneous removal of the blocking group to produce alkyl L-ristosaminides.

2. The process of claim 1 wherein step (f) comprises reacting the compound produced by step (e) with a blocking agent to produce a compound having the formula

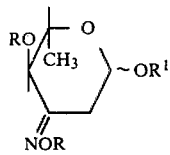

wherein R is a blocking group, and then reducing the resultant compound with simultaneous removal of the blocking groups to produce alkyl L-ristosaminides.

3. The process of claim 2 wherein L-rhamnal is prepared by deacetylating 3,4-di-O-acetyl-L-rhamnal.

4. The process of claim 2 wherein alkyl L-ristosaminides are converted to N-benzoyl-L-ristosamine by a method comprising benzoylating alkyl L-ristosaminides; and subjecting the resultant alkyl N-benzoyl-L-ristosaminide to acid hydrolysis to produce N-benzoyl-L-ristosamine.

5. A process for producing 1,5-anhydro-3-oxo-2,3,6-trideoxy-L-erythro-hex-1-enitol comprising oxidizing either L-rhamnal or 6-deoxy-L-allal.

6. A process for producing 1,5-anhydro-3-oxo-4-O-acetyl-2,3,6-trideoxy-L-erythro-hex-1-enitol comprising acetylating 1,5-anhydro-3-oxo-2,3,6-trideoxy-L-erythro-hex-1-enitol.

7. A process for producing methyl 2-chloromercuri-3-oxo-4-O-acetyl-2,3,6-trideoxy-L-(ribo, arabino)-hexopyranoside comprising subjecting 1,5-anhydro-3-oxo-4-O-acetyl-2,3,6-trideoxy-L-erythro-hex-1-enitol to methoxymercuration.

8. A process for producing methyl 2-chloromercuri-3-oximino-4-O-acetyl-2,3,6-trideoxy-L-(ribo, arabino)-hexopyranoside comprising subjecting methyl 2-chloromercuri-3-oxo-4-O-acetyl-2,3,6-trideoxy-L-(ribo, arabino)-hexopyranoside to oximation.

9. A process for producing methyl 3-oximino-4-O-acetyl-2,3,6-trideoxy-L-erythro-hexopyranoside comprising demercurating methyl 2-chloromercuri-3-oximino-4-O-acetyl-2,3,6-trideoxy-L-(ribo, arabino)-hexopyranoside.

10. A process for producing methyl 3-acetyloximino-4-O-acetyl-2,3,6-trideoxy-L-erythro-hexopyranoside comprising acetylating methyl 3-oximino-4-O-acetyl-2,3,6-trideoxy-L-erythro-hexopyranoside.

11. A process for producing methyl L-ristosaminide comprising reducing methyl 3-acetyloximino-4-O-acetyl-2,3,6-tri-deoxy-L-erythro-hexopyranoside with simultaneous deacetylation.

12. A compound having the formula

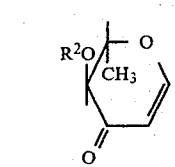

wherein $R^2$ is

13. The compound of claim 12 wherein $R^2$ is H.
14. The compound of claim 12 wherein $R^2$ is

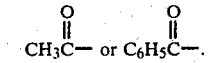

15. A compound having the formula

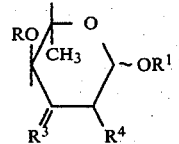

wherein
R is

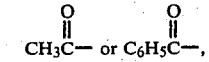

$R^1$ is $C_1$-$C_6$ alkyl
$R^3$ is

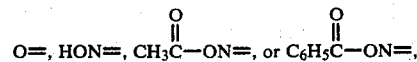

$R^4$ is HgCl or H provided that when $R^4$ is HgCl, $R^3$ must be O= or HON=; when $R^4$ is H, $R^3$ cannot be O=.

16. The compound of claim 15 wherein $R^3$ is O= and $R^4$ is HgCl.
17. The compound of claim 15 wherein $R^3$ is HON= and $R^4$ is HgCl.
18. The compound of claim 15 wherein $R^3$ is HON= and $R^4$ is H.
19. The compound of claim 15 wherein $R^3$ is

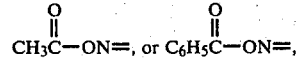

and $R^4$ is H.

* * * * *